US010324014B2

(12) United States Patent
Feng et al.

(10) Patent No.: US 10,324,014 B2
(45) Date of Patent: Jun. 18, 2019

(54) LOW-FREQUENCY DISTURBANCE AND HIGH-SPEED IMPACT TYPE HIGH-PRESSURE TRUE TRIAXIAL TEST APPARATUS AND METHOD

(71) Applicant: Northeastern University, Shenyang, Liaoning Province (CN)

(72) Inventors: Xia ting Feng, Shenyang (CN); Xi wei Zhang, Shenyang (CN); Rui Kong, Shenyang (CN); Cheng xiang Yang, Shenyang (CN); Dong hui Ma, Changchun (CN); Shuai Peng, Shenyang (CN); Lei Shi, Shenyang (CN); Zhi bin Yao, Shenyang (CN); Jun Tian, Shenyang (CN)

(73) Assignee: NORTHEASTERN UNIVERSITY, Shenyang, Liaoning Province (CN)

( * ) Notice: Subject to any disclaimer, the term of this patent is extended or adjusted under 35 U.S.C. 154(b) by 155 days.

(21) Appl. No.: 15/558,958

(22) PCT Filed: Mar. 28, 2017

(86) PCT No.: PCT/CN2017/078368
§ 371 (c)(1),
(2) Date: Sep. 15, 2017

(87) PCT Pub. No.: WO2018/170933
PCT Pub. Date: Sep. 27, 2018

(65) Prior Publication Data
US 2018/0275034 A1  Sep. 27, 2018

(30) Foreign Application Priority Data
Mar. 24, 2017 (CN) .......................... 2017 1 0183372

(51) Int. Cl.
*G01N 3/307* (2006.01)
*G01M 7/08* (2006.01)

(52) U.S. Cl.
CPC .............. *G01N 3/307* (2013.01); *G01M 7/08* (2013.01); *G01N 2203/0055* (2013.01);
(Continued)

(58) Field of Classification Search
CPC .......... G01N 3/307; G01N 2203/0067; G01N 2203/0055; G01N 2203/0232; G01N 2203/0098; G01M 7/08
See application file for complete search history.

(56) References Cited

U.S. PATENT DOCUMENTS 5,025,668 A * 6/1991 Sarda ........................ G01N 3/10
73/795
7,320,242 B2 * 1/2008 Hoo Fatt .................. G01N 3/30
73/12.14
(Continued)

FOREIGN PATENT DOCUMENTS

CN 101458192 A 6/2009
CN 102331366 A 1/2012
(Continued)

*Primary Examiner* — Freddie Kirkland, III
(74) *Attorney, Agent, or Firm* — Muncy, Geissler, Olds & Lowe, P.C.

(57) ABSTRACT

A high-pressure true triaxial test apparatus with capacity of low-frequency disturbance and high-speed impact includes static and dynamic loading frames, four static loading actuators, two dynamic loading actuators and an SHPB mechanism, wherein all actuators are connected with a hydraulic station system; a hollow way is formed in the axial center of each piston shaft of the dynamic loading actuators, a dynamic pressure sensor adopting a hollow ring structure is mounted at the end part of each piston shaft, and the SHPB mechanism applies a high-speed impact load on a rock sample through the dynamic pressure sensors respectively;
(Continued)

and the dynamic loading actuators adopt a static pressure oilway balance support sealing manner and are connected with the hydraulic station system, each oilway is provided with an energy accumulator, and flow is increased by the servo valves to drive pistons to perform dynamic response.

5 Claims, 3 Drawing Sheets

(52) U.S. Cl.
CPC .............. *G01N 2203/0067* (2013.01); *G01N 2203/0098* (2013.01); *G01N 2203/0232* (2013.01)

(56) References Cited

U.S. PATENT DOCUMENTS

| | | | |
|---|---|---|---|
| 9,410,874 B2 * | 8/2016 | He | G01N 3/313 |
| 9,880,081 B1 * | 1/2018 | Gupta | G01N 3/08 |
| 10,197,483 B2 * | 2/2019 | Du | G01N 3/24 |
| 2019/0033198 A1 * | 1/2019 | Atapour | G01N 15/0806 |

FOREIGN PATENT DOCUMENTS

| | | |
|---|---|---|
| CN | 202101910 U | 1/2012 |
| CN | 102735532 A | 10/2012 |
| CN | 202837121 U | 3/2013 |
| CN | 103481914 A | 1/2014 |
| CN | 104535409 A | 4/2015 |
| CN | 105169069 A | 12/2015 |
| CN | 106198264 A | 12/2016 |
| JP | 2000046707 A | 2/2000 |

* cited by examiner

LOW-FREQUENCY DISTURBANCE AND HIGH-SPEED IMPACT TYPE HIGH-PRESSURE TRUE TRIAXIAL TEST APPARATUS AND METHOD

BACKGROUND OF THE INVENTION

1. Field of the Invention

The present invention belongs to the technical field of laboratory rock mechanic tests and particularly relates to a low-frequency disturbance and high-speed impact type high-pressure true triaxial test apparatus and method.

2. The Prior Arts

Deep rock masses are carriers of deep hydraulic and hydropower engineering, deep metal ore mining engineering, engineering of a high-level radioactive waste repository and the like. After engineering excavation is carried out on the deep rock masses, the deep rock masses are subjected to blasting disturbance and damage impact. Therefore, a series of instable failure and even geological disasters sometimes, such as zonal rupture, time-lag rock burst, impact type mine pressure, and impact type rock burst, can be induced. The deep rock masses show phenomena of critical fracture and dynamic instability due to the actions of dynamic loads and static loads caused by the blasting damage, blasting vibration, rock burst shock waves and the like.

At present, in the research on an inducement mechanism of failure and instability for the deep rock masses under the three-dimensional high geo-stress, the inducement mechanism of the actions of perturbation and impact for the disasters of the deep rock masses remains unknown, and basic research achievements are seriously insufficient. In view of the environment of the three-dimensional high geo-stress of the deep rock masses, relevant test researches need to be conducted under a true triaxial condition. In consideration of the action of the dynamic loads, such as impact of blasting vibration, the high-frequency component of the action can reach the megahertz grade, while high-speed impact often results in damage to rocks under a high strain rate, and impact waves in the rock masses can also form 1 Hz-100 Hz of low-frequency disturbance due to oscillation and attenuation, resulting in damage to the rock masses under a medium and low strain rate. Therefore, it is urgent to understand inducement mechanisms of critical fracture and dynamic instability of the rocks under the action of the dynamic loads from the high strain rate to the medium and low strain rate, so as to meet the research requirement for deep engineering rock mechanics.

However, in laboratory rock mechanic tests for the research on the critical fracture and the dynamic instability of the deep rock masses at the present stage, a low-frequency disturbance test of the rocks are mostly concentrated on a basis of a uniaxial or a conventional triaxis apparatus, and the three-dimensional high geo-stress state of a true environment cannot be simulated. Besides, the applied disturbance frequency can only reach the maximum value of about 10 Hz due to the restriction of attenuation and friction factors of actuators, so that the range of the disturbance frequency cannot be further expanded. Additionally, a high strain rate impact test of the rocks based on an SHPB (Split Hopkinson Pressure Bar) technology goes through a high strain rate impact test of the rocks without the static loads, a high strain rate impact test of the rocks under a confining pressure condition and a high strain rate impact test of the rocks under 'confining pressure and axial pressure' conditions respectively, but a high strain rate impact test of the rocks under a true triaxial static load condition has not been reported so far.

Therefore, in order to better understand the inducement mechanisms of the critical fracture and the dynamic instability of the rocks under the action of the dynamic loads from the high strain rate to the medium and low strain rate, it is very necessary to research and develop a set of low-frequency disturbance and high-speed impact type true triaxial test equipment.

SUMMARY OF THE INVENTION

For the problems existing in the prior art, the present invention provides a low-frequency disturbance and high-speed impact type high-pressure true triaxial test apparatus and method, so that a high strain rate impact test of rocks under a true triaxial static load condition is realized for the first time. Besides, requirements of a low-frequency disturbance test of the rocks under a true triaxial condition can also be met, and the maximum disturbance frequency can reach 50 Hz. Therefore, a gap of the research field on the inducement mechanisms of failure and instability of deep rock masses under three-dimensional high geo-stress is filled, and the research range on deep engineering rock mechanics is further extended.

In order to realize the purpose, the present invention adopts the following technical scheme. The low-frequency disturbance and high-speed impact type high-pressure true triaxial test apparatus includes a static loading frame, a dynamic loading frame, a first vertical static loading actuator, a second vertical static loading actuator, a first horizontal static loading actuator, a second horizontal static loading actuator, a first horizontal dynamic loading actuator, a second horizontal dynamic loading actuator and an SHPB (Split Hopkinson Pressure Bar) mechanism, wherein, the first vertical static loading actuator, the second vertical static loading actuator, the first horizontal static loading actuator, the second horizontal static loading actuator, the first horizontal dynamic loading actuator and the second horizontal dynamic loading actuator are connected with a hydraulic station system.

The static loading frame adopts a square structure, the square center of the static loading frame is a rock sample loading position, and the static loading frame is fixedly mounted on ground by a first base; the first vertical static loading actuator and the second vertical static loading actuator are symmetrically arranged on an upper beam and a lower beam of the static loading frame, and the first horizontal static loading actuator and the second horizontal static loading actuator are symmetrically arranged on a front upright column and a rear upright column of the static loading frame.

A second base and a third base are respectively arranged on ground on the left side and the right side of the static loading frame, and the dynamic loading frame passes through a central hole of the static loading frame and is seated on the second base and the third base; two guide rails are respectively arranged on the second base and the third base, guide wheels are mounted at the bottom of the static loading frame, and the static loading frame is in sliding fit with the guide rails by the guide wheels; the first horizontal dynamic loading actuator and the second horizontal dynamic loading actuator are symmetrically arranged at the left end and the right end of the dynamic loading frame.

A static pressure sensor is mounted at the end part of each of piston shafts of the first vertical static loading actuator, the second vertical static loading actuator, the first horizontal static loading actuator and the second horizontal static loading actuator.

A first hollow way is formed in the axial center of a piston shaft of the first horizontal dynamic loading actuator, a second hollow way is formed in the axial center of a piston shaft of the second horizontal dynamic loading actuator, a dynamic pressure sensor is mounted at the end part of each of the piston shafts of the first horizontal dynamic loading actuator and the second horizontal dynamic loading actuator, each of the dynamic pressure sensors adopts a hollow ring structure, and central holes of the dynamic pressure sensors, the first hollow way and the second hollow way are coaxially formed.

The SHPB mechanism applies a high-speed impact load on a rock sample through the first hollow way, the central holes of the dynamic pressure sensors and the second hollow way respectively.

The SHPB mechanism includes an emitter, an impact bar, an incident bar, a transmission bar, an absorption bar and an absorber, wherein strain gages are attached on the surfaces of the incident bar and the transmission bar; the emitter is arranged on the ground by a fourth base, the impact bar is arranged on the fourth base by a support frame, and one end of the impact bar is connected with the emitter; the incident bar is located in the first hollow way; the absorber is arranged on the ground by a fifth base, the absorption bar is arranged on the fifth base by a support frame, and the transmission bar is located in the second hollow way; and the impact bar, the incident bar, the transmission bar and the absorption bar are coaxially arranged.

The first horizontal dynamic loading actuator and the second horizontal dynamic loading actuator adopt the same structures and adopt a static pressure oilway balance support sealing manner, oil chambers on one sides of the actuators are connected with the hydraulic station system by a first servo valve, and an oilway on the side is provided with a first energy accumulator; an oil chamber on the other sides of the actuators is connected with the hydraulic station system by a second servo valve, and an oilway on the side is provided with a second energy accumulator; and flow is increased by the first servo valve and the second servo valve, so as to drive a piston to perform dynamic response, and system pressure during low-frequency disturbance loading is balanced by the first energy accumulator and the second energy accumulator.

A test method adopting the low-frequency disturbance and high-speed impact type high-pressure true triaxial test apparatus includes the following steps.

Step I: completing packaging for the rock sample by a rigid pressing block and enabling a displacement sensor to be mounted between the rigid pressing block and the rock sample.

Step II: pushing the dynamic loading frame out of the central hole of the static loading frame and enabling the packaged rock sample to be fixedly mounted in the dynamic loading frame.

Step III: adjusting the position of the displacement sensor and the elongation of a contact probe so that the displacement sensor is located within the measuring range of a test.

Step IV: pushing the dynamic loading frame on which the rock sample back is fixed into the central hole of the static loading frame so that the rock sample is located in the center of three-way loading.

Step V: completing accurate clamping for the rock sample in a centering manner by implementing displacement control on the first vertical static loading actuator, the second vertical static loading actuator, the first horizontal static loading actuator, the second horizontal static loading actuator, the first horizontal dynamic loading actuator and the second horizontal dynamic loading actuator.

Step VI: performing true triaxial static loading on the rock sample by the first vertical static loading actuator, the second vertical static loading actuator, the first horizontal static loading actuator, the second horizontal static loading actuator, the first horizontal dynamic loading actuator and the second horizontal dynamic loading actuator.

Step VII: keeping the stress level of the true triaxial static loading unchanged when at a target stress level value, applying an in-phase centering low-frequency disturbance load on the rock sample by the first horizontal dynamic loading actuator and the second horizontal dynamic loading actuator and applying the high-speed impact load on the rock sample by the SHPB mechanism.

Step VIII: recording and observing deformation situations of the rock sample.

The step VII includes three applying methods of low-frequency disturbance and high-speed impact: the first manner: independently applying the low-frequency disturbance load, the second manner: independently applying the high-speed impact load, and the third manner: applying the low-frequency disturbance load and then applying the high-speed impact load.

The low-frequency disturbance and high-speed impact type high-pressure true triaxial test apparatus and method disclosed by the present invention provide the following beneficial effects.

A high strain rate impact test of rocks under a true triaxial static load condition is realized for the first time, besides, requirements of a low-frequency disturbance test of the rocks under a true triaxial condition can also be met, and the maximum disturbance frequency can reach 50 Hz; and therefore, a gap of the research field on the inducement mechanisms of failure and instability of deep rock masses under three-dimensional high geo-stress is filled, and the research range on deep engineering rock mechanics is further extended.

Applying methods of low-frequency disturbance and high-speed impact can be freely set on the same equipment, in the whole process of conducting the stress strain of the rocks, any post-peak state can be maintained for a certain time, and besides, different-frequency dynamic disturbance and damage tests can be conducted many times based on this.

Horizontal dynamic loading actuators provided by the present invention adopt a balance support sealing manner of a static oilway, thereby reducing frictional force to the maximum extent; flow of hydraulic oil is increased by double servo valves, thereby effectively increasing the start speed of pistons of the actuators; and hollow ways formed in piston shafts are served as ways for the high strain rate impact tests of the SHPB mechanism, and through the hollow ways, the self weight of the piston shafts is also effectively lightened.

BRIEF DESCRIPTION OF THE DRAWINGS

The present invention will be apparent to those skilled in the art by reading the following detailed description of a preferred embodiment thereof, with reference to the attached drawings, in which.

In drawings: 1—static loading frame, 2—dynamic loading frame, 3—first vertical static loading actuator, 4—second vertical static loading actuator, 5—first horizontal static loading actuator, 6—second horizontal static loading actuator, 7—first horizontal dynamic loading actuator, 8—second horizontal dynamic loading actuator, 9—first base, 10—second base, 11—third base, 12—guide rail, 13—guide wheel, 14—static pressure sensor, 15—first hollow way, 16—second hollow way, 17—dynamic pressure sensor, 18—emitter, 19—impact bar, 20—incident bar, 21—transmission bar, 22—absorption bar, 23—absorber, 24—fourth base, 25—fifth base, 26—rock sample.

DETAILED DESCRIPTION OF THE PREFERRED EMBODIMENTS

The accompanying drawings are included to provide a further understanding of the invention, and are incorporated in and constitute a part of this specification. The drawings illustrate embodiments of the invention and, together with the description, serve to explain the principles of the invention.

Figure 1:
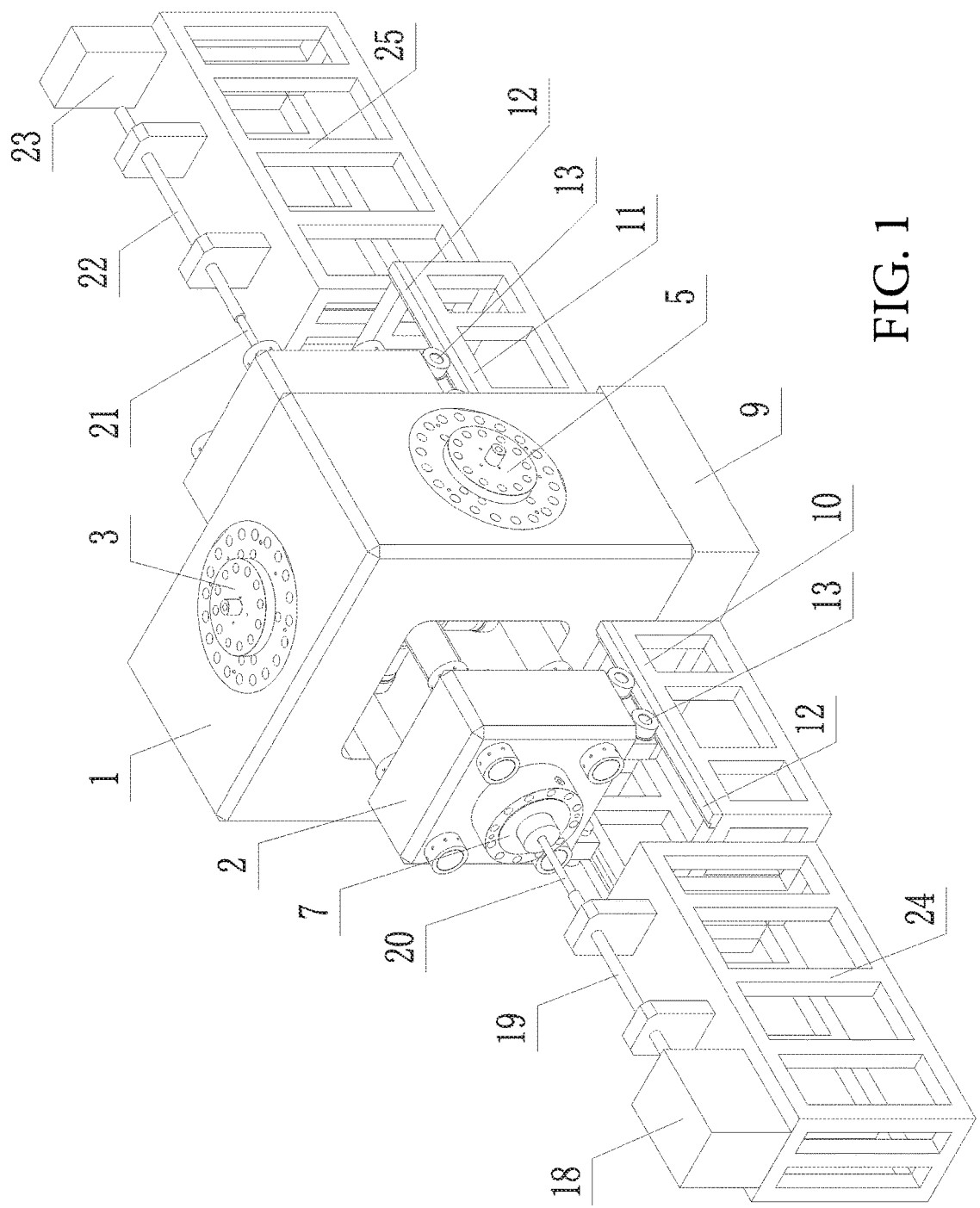
FIG. 1 is a block diagram of a low-frequency disturbance and high-speed impact type high-pressure true triaxial test apparatus and method of the present invention.
Figure 2:
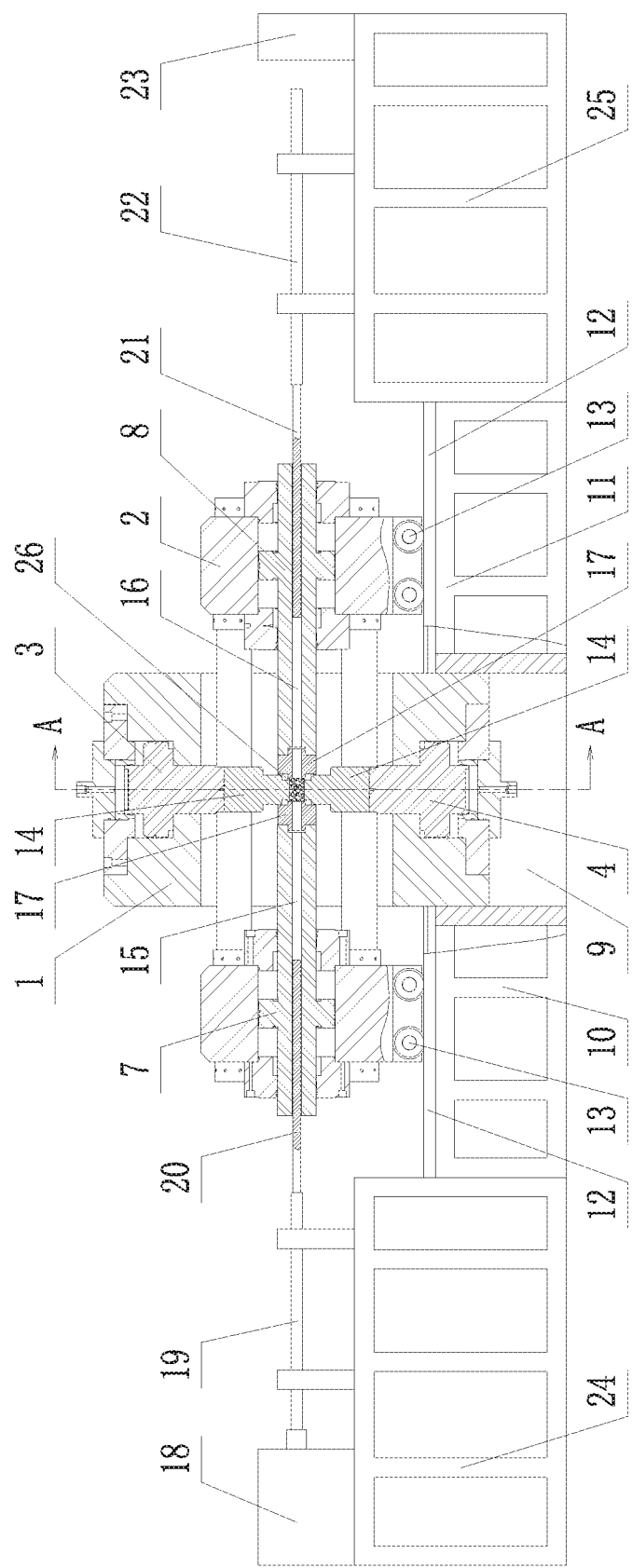
FIG. 2 is a front view of a low-frequency disturbance and high-speed impact type high-pressure true triaxial test apparatus and method of the present invention.
Figure 3:
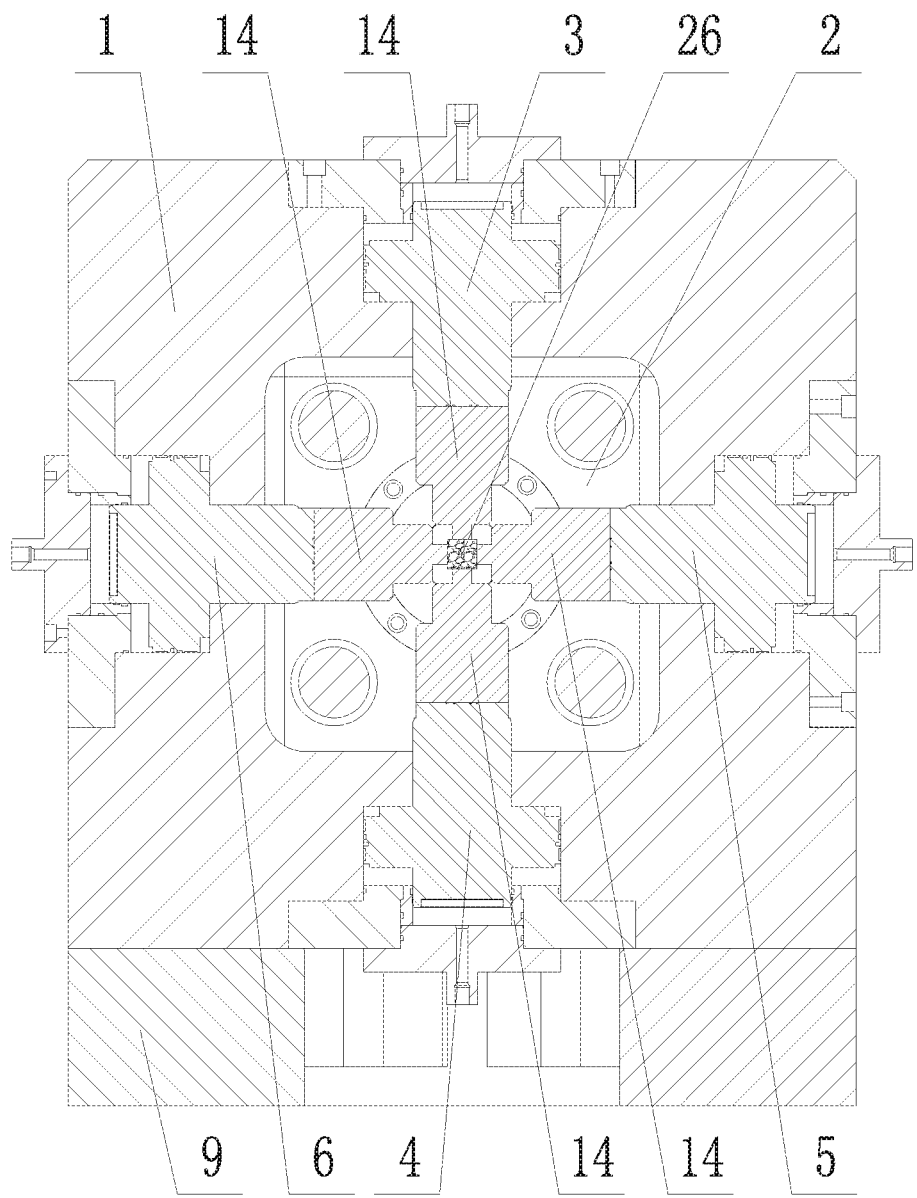
FIG. 3 is an A-A section view of FIG. 2.

As shown in FIGS. 1-3, a low-frequency disturbance and high-speed impact type high-pressure true triaxial test apparatus includes a static loading frame 1, a dynamic loading frame 2, a first vertical static loading actuator 3, a second vertical static loading actuator 4, a first horizontal static loading actuator 5, a second horizontal static loading actuator 6, a first horizontal dynamic loading actuator 7, a second horizontal dynamic loading actuator 8 and an SHPB (Split Hopkinson Pressure Bar) mechanism, wherein, the first vertical static loading actuator 3, the second vertical static loading actuator 4, the first horizontal static loading actuator 5, the second horizontal static loading actuator 6, the first horizontal dynamic loading actuator 7 and the second horizontal dynamic loading actuator 8 are connected with a hydraulic station system.

The static loading frame 1 adopts a square structure, the square center of the static loading frame 1 is a rock sample loading position, and the static loading frame 1 is fixedly mounted on ground by a first base 9; the first vertical static loading actuator 3 and the second vertical static loading actuator 4 are symmetrically arranged on an upper beam and a lower beam of the static loading frame 1, and the first horizontal static loading actuator 5 and the second horizontal static loading actuator 6 are symmetrically arranged on a front upright column and a rear upright column of the static loading frame 1.

A second base 10 and a third base 11 are respectively arranged on ground on the left side and the right side of the static loading frame 1, and the dynamic loading frame 2 passes through a central hole of the static loading frame 1 and is seated on the second base 10 and the third base 11; two guide rails 12 are respectively arranged on the second base 10 and the third base 11, guide wheels 13 are mounted at the bottom of the static loading frame 1, and the static loading frame 1 is in sliding fit with the guide rails 13 by the guide wheels 12; the first horizontal dynamic loading actuator 7 and the second horizontal dynamic loading actuator 8 are symmetrically arranged at the left end and the right end of the dynamic loading frame 2.

A static pressure sensor 14 is mounted at the end part of each of piston shafts of the first vertical static loading actuator 3, the second vertical static loading actuator 4, the first horizontal static loading actuator 5 and the second horizontal static loading actuator 6.

A first hollow way 15 is formed in the axial center of a piston shaft of the first horizontal dynamic loading actuator 7, a second hollow way 16 is formed in the axial center of a piston shaft of the second horizontal dynamic loading actuator 8, a dynamic pressure sensor 17 is mounted at the end part of each of the piston shafts of the first horizontal dynamic loading actuator 7 and the second horizontal dynamic loading actuator 8, each of the dynamic pressure sensors 17 adopts a hollow ring structure, and central holes of the dynamic pressure sensors 17, the first hollow way 15 and the second hollow way 16 are coaxially formed.

The SHPB mechanism applies a high-speed impact load on a rock sample 26 through the first hollow way 15, the central holes of the dynamic pressure sensors 17 and the second hollow way 16 respectively.

The SHPB mechanism includes an emitter 18, an impact bar 19, an incident bar 20, a transmission bar 21, an absorption bar 22 and an absorber 23, wherein strain gages are attached on the surfaces of the incident bar 20 and the transmission bar 21; the emitter 18 is arranged on the ground by a fourth base 24, the impact bar 19 is arranged on the fourth base 24 by a support frame, and one end of the impact bar 19 is connected with the emitter 18; the incident bar 20 is located in the first hollow way 15; the absorber 23 is arranged on the ground by a fifth base 25, the absorption bar 22 is arranged on the fifth base 25 by a support frame, and the transmission bar 21 is located in the second hollow way 16; and the impact bar 19, the incident bar 20, the transmission bar 21 and the absorption bar 22 are coaxially arranged.

The first horizontal dynamic loading actuator 7 and the second horizontal dynamic loading actuator 8 adopt the same structures and adopt a static pressure oilway balance support sealing manner, oil chambers on one sides of the actuators are connected with the hydraulic station system by a first servo valve, and an oilway on the side is provided with a first energy accumulator; an oil chamber on the other sides of the actuators is connected with the hydraulic station system by a second servo valve, and an oilway on the side is provided with a second energy accumulator; and flow is increased by the first servo valve and the second servo valve, so as to drive a piston to perform dynamic response, and system pressure during low-frequency disturbance loading is balanced by the first energy accumulator and the second energy accumulator.

A test method adopting the low-frequency disturbance and high-speed impact type high-pressure true triaxial test apparatus includes the following steps.

Step I: completing packaging for the rock sample 26 by a rigid pressing block and enabling a displacement sensor to be mounted between the rigid pressing block and the rock sample 26.

Step II: pushing the dynamic loading frame 2 out of the central hole of the static loading frame 1 and enabling the packaged rock sample 26 to be fixedly mounted in the dynamic loading frame 2.

Step III: adjusting the position of the displacement sensor and the elongation of a contact probe, so that the displacement sensor is located within the measuring range of a test.

Step IV: pushing the dynamic loading frame 2 on which the rock sample back 26 is fixed into the central hole of the static loading frame 1, so that the rock sample 26 is located in the center of three-way loading.

Step V: completing accurate clamping for the rock sample 26 in a centering manner by implementing displacement control on the first vertical static loading actuator 3, the second vertical static loading actuator 4, the first horizontal static loading actuator 5, the second horizontal static loading actuator 6, the first horizontal dynamic loading actuator 7 and the second horizontal dynamic loading actuator 8.

Step VI: performing true triaxial static loading on the rock sample 26 by the first vertical static loading actuator 3, the second vertical static loading actuator 4, the first horizontal static loading actuator 5, the second horizontal static loading actuator 6, the first horizontal dynamic loading actuator 7 and the second horizontal dynamic loading actuator 8.

Step VII: keeping the stress level of the true triaxial static loading unchanged when at a target stress level value, applying an in-phase centering low-frequency disturbance load on the rock sample 26 by the first horizontal dynamic loading actuator 7 and the second horizontal dynamic loading actuator 8 and applying the high-speed impact load on the rock sample 26 by the SHPB mechanism, wherein the step VII comprises three applying methods of low-frequency disturbance and high-speed impact: the first manner: independently applying the low-frequency disturbance load, the second manner: independently applying the high-speed impact load, and the third manner: applying the low-frequency disturbance load and then applying the high-speed impact load.

Step VIII: recording and observing deformation situations of the rock sample 26.

The scheme in the embodiment is not intended to limit the patent protection scope of the present invention, and any equivalent implementation or change made without departing from the present invention shall be included in the scope of the patent of the scheme.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A low-frequency disturbance and high-speed impact type high-pressure true triaxial test apparatus, comprising:
    a static loading frame, a dynamic loading frame, a first vertical static loading actuator, a second vertical static loading actuator, a first horizontal static loading actuator, a second horizontal static loading actuator, a first horizontal dynamic loading actuator, a second horizontal dynamic loading actuator and an SHPB (Split Hopkinson Pressure Bar) mechanism, wherein the first vertical static loading actuator, the second vertical static loading actuator, the first horizontal static loading actuator, the second horizontal static loading actuator, the first horizontal dynamic loading actuator and the second horizontal dynamic loading actuator are connected with a hydraulic station system;
    the static loading frame adopts a square structure, the square center of the static loading frame is a rock sample loading position, and the static loading frame is fixedly mounted on ground by a first base; the first vertical static loading actuator and the second vertical static loading actuator are symmetrically arranged on an upper beam and a lower beam of the static loading frame, and the first horizontal static loading actuator and the second horizontal static loading actuator are symmetrically arranged on a front upright column and a rear upright column of the static loading frame;
    a second base and a third base are respectively arranged on ground on the left side and the right side of the static loading frame, and the dynamic loading frame passes through a central hole of the static loading frame and is seated on the second base and the third base; two guide rails are respectively arranged on the second base and the third base, guide wheels are mounted at the bottom of the static loading frame, and the static loading frame is in sliding fit with the guide rails by the guide wheels; the first horizontal dynamic loading actuator and the second horizontal dynamic loading actuator are symmetrically arranged at the left end and the right end of the dynamic loading frame;
    a static pressure sensor is mounted at the end part of each of piston shafts of the first vertical static loading actuator, the second vertical static loading actuator, the first horizontal static loading actuator and the second horizontal static loading actuator;
    a first hollow way is formed in the axial center of a piston shaft of the first horizontal dynamic loading actuator, a second hollow way is formed in the axial center of a piston shaft of the second horizontal dynamic loading actuator, a dynamic pressure sensor is mounted at the end part of each of the piston shafts of the first horizontal dynamic loading actuator and the second horizontal dynamic loading actuator, each of the dynamic pressure sensors adopts a hollow ring structure, and central holes of the dynamic pressure sensors, the first hollow way and the second hollow way are coaxially formed; and
    the SHPB mechanism applies a high-speed impact load on a rock sample through the first hollow way, the central holes of the dynamic pressure sensors and the second hollow way respectively.

2. The low-frequency disturbance and high-speed impact type high-pressure true triaxial test apparatus according to claim 1, wherein, the SHPB mechanism includes an emitter, an impact bar, an incident bar, a transmission bar, an absorption bar and an absorber, wherein strain gages are attached on the surfaces of the incident bar and the transmission bar; the emitter is arranged on the ground by a fourth base, the impact bar is arranged on the fourth base by a support frame, and one end of the impact bar is connected with the emitter; the incident bar is located in the first hollow way; the absorber is arranged on the ground by a fifth base, the absorption bar is arranged on the fifth base by a support frame, and the transmission bar is located in the second hollow way; and the impact bar, the incident bar, the transmission bar and the absorption bar are coaxially arranged.

3. The low-frequency disturbance and high-speed impact type high-pressure true triaxial test apparatus according to claim 1, wherein, the first horizontal dynamic loading actuator and the second horizontal dynamic loading actuator adopt the same structures and adopt a static pressure oilway balance support sealing manner, oil chambers on one sides of the actuators are connected with the hydraulic station system by a first servo valve, and an oilway on the side is provided with a first energy accumulator; an oil chamber on the other sides of the actuators is connected with the hydraulic station system by a second servo valve, and an oilway on the side is provided with a second energy accumulator; and flow is increased by the first servo valve and the second servo valve, so as to drive a piston to perform dynamic response, and system pressure during low-frequency disturbance loading is balanced by the first energy accumulator and the second energy accumulator.

4. A test method adopting the low-frequency disturbance and high-speed impact type high-pressure true triaxial test apparatus according to claim 1, comprising the following steps:
- step I: completing packaging for the rock sample by a rigid pressing block and enabling a displacement sensor to be mounted between the rigid pressing block and the rock sample;
- step II: pushing the dynamic loading frame out of the central hole of the static loading frame and enabling the packaged rock sample to be fixedly mounted in the dynamic loading frame;
- step III: adjusting the position of the displacement sensor and the elongation of a contact probe, so that the displacement sensor is located within the measuring range of a test;
- step IV: pushing the dynamic loading frame on which the rock sample back is fixed into the central hole of the static loading frame, so that the rock sample is located in the center of three-way loading;
- step V: completing accurate clamping for the rock sample in a centering manner by implementing displacement control on the first vertical static loading actuator, the second vertical static loading actuator, the first horizontal static loading actuator, the second horizontal static loading actuator, the first horizontal dynamic loading actuator and the second horizontal dynamic loading actuator;
- step VI: performing true triaxial static loading on the rock sample by the first vertical static loading actuator, the second vertical static loading actuator, the first horizontal static loading actuator, the second horizontal static loading actuator, the first horizontal dynamic loading actuator and the second horizontal dynamic loading actuator;
- step VII: keeping the stress level of the true triaxial static loading unchanged when at a target stress level value, applying an in-phase centering low-frequency disturbance load on the rock sample by the first horizontal dynamic loading actuator and the second horizontal dynamic loading actuator and applying the high-speed impact load on the rock sample by the SHPB mechanism; and
- step VIII: recording and observing deformation situations of the rock sample.

5. The test method according to claim 4, wherein, the step VII includes three applying methods of low-frequency disturbance and high-speed impact: the first manner: independently applying the low-frequency disturbance load, the second manner: independently applying the high-speed impact load, and the third manner: applying the low-frequency disturbance load and then applying the high-speed impact load.

* * * * *